(12) United States Patent
Black et al.

(10) Patent No.: US 10,945,775 B2
(45) Date of Patent: Mar. 16, 2021

(54) LOCKING BONE SCREWS AND METHODS OF USE THEREOF

(71) Applicant: GLOBUS MEDICAL, INC., Audubon, PA (US)

(72) Inventors: Michael Black, Phoenixville, PA (US); Jon Suh, Ambler, PA (US)

(73) Assignee: Globus Medical Inc., Audubon, PA (US)

( * ) Notice: Subject to any disclaimer, the term of this patent is extended or adjusted under 35 U.S.C. 154(b) by 36 days.

(21) Appl. No.: 16/243,599

(22) Filed: Jan. 9, 2019

(65) Prior Publication Data

US 2019/0142484 A1 May 16, 2019

Related U.S. Application Data

(63) Continuation of application No. 14/956,791, filed on Dec. 2, 2015, now Pat. No. 10,206,726, which is a continuation of application No. 14/147,173, filed on Jan. 3, 2014, now Pat. No. 9,226,785, which is a continuation of application No. 12/771,375, filed on Apr. 30, 2010, now Pat. No. 8,647,371.

(51) Int. Cl.
*A61B 17/80* (2006.01)
*A61B 17/86* (2006.01)

(52) U.S. Cl.
CPC ...... *A61B 17/8052* (2013.01); *A61B 17/8038* (2013.01); *A61B 17/8042* (2013.01); *A61B 17/8605* (2013.01); *A61B 17/8615* (2013.01); *A61B 17/8685* (2013.01)

(58) Field of Classification Search
CPC .................. A61B 17/8685; A61B 17/8038
See application file for complete search history.

(56) References Cited

U.S. PATENT DOCUMENTS

| | | | |
|---|---|---|---|
| 5,169,400 A * | 12/1992 | Muhling | A61B 17/86 411/395 |
| 5,275,601 A | 1/1994 | Gogolewski et al. | |
| 7,063,701 B2 * | 6/2006 | Michelson | A61B 17/866 606/307 |
| 7,846,190 B2 * | 12/2010 | Ball | A61B 17/8038 606/313 |
| 8,496,692 B2 | 7/2013 | Bhatnagar et al. | |
| 8,840,650 B2 | 9/2014 | Cawley | |

* cited by examiner

*Primary Examiner* — Anu Ramana

(57) ABSTRACT

The invention encompasses a bone screw for use in the human body including a shaft having a threaded region along at least a portion of its length and a screw head including a locking mechanism to secure the screw, for example to a bone plate. In certain embodiments, the thread has an outer diameter dimensioned to pass through the screw hole in the implant. The screw head is configured to cooperatively engage at least a portion of the screw hole of the implant so as to prevent the screw from coming out of the implant and avoided soft tissue damage and other complications associated with unintended screw removal.

16 Claims, 12 Drawing Sheets

LOCKING BONE SCREWS AND METHODS OF USE THEREOF

CROSS-REFERENCE TO RELATED APPLICATIONS

The present application is a continuation of U.S. patent application Ser. No. 14/956,791, filed on Dec. 2, 2015, now U.S. Pat. No. 10,206,726, which is a continuation of U.S. patent application Ser. No. 14/147,173, filed on Jan. 3, 2014, now U.S. Pat. No. 9,226,785, which is a continuation of U.S. patent application Ser. No. 12/771,375, filed on Apr. 30, 2010 now U.S. Pat. No. 8,647,371, all of which are incorporated by reference herein in their entireties for all purposes.

FIELD OF THE INVENTION

The invention encompasses a bone screw for use in the human body including a shaft having a threaded region along at least a portion of its length and a screw head including a locking mechanism to secure the screw, for example to a bone plate. In certain embodiments, the thread has an outer diameter dimensioned to pass through the screw hole in the implant. The screw head is configured to cooperatively engage at least a portion of the screw hole of the implant so as to prevent the screw from coming out of the implant and avoided soft tissue damage and other complications associated with unintended screw removal.

BACKGROUND OF THE INVENTION

Many surgical procedures require securing an implant to bone, for example, to vertebrae along the spine. Orthopedic fixation devices are frequently coupled to bone by the use of fasteners such as screws, threaded bolts, or pins. For example, bone plates can be secured to bone with bone screws, inserted through plate holes.

Securing the screws to the plate provides a fixed angle relationship between the plate and screw and reduces the incidence of loosening. Current techniques involve a locking screw that has threading on an outer surface of its head that matches with corresponding threading on the surface of a plate hole to lock the screw to the plate. Bone plates having threaded holes for accommodating locking screws are used with such screws.

For example, as a screw is being inserted into bone through the bushing and plate hole, a threaded tapered head of the screw engages a threaded internal surface of the bushing to expand the bushing against the wall of the plate hole, thereby friction locking the screw at the desired angular orientation with respect to the plate.

These multi-component traditional plate assemblies can be cumbersome and tedious to manipulate during surgery to achieve the most desirable angle for directing the bone screw into the patient.

The inventors have developed bone screws with locking mechanisms to provide retention of the screws with a bone plate and/or with the bone to prevent movement or unintended removal of the screw from the plate.

SUMMARY OF THE INVENTION

The invention generally encompasses bone screws including a screw head and a proximal shaft adapted to be secured to a bone, wherein the screw head comprises a plurality of flexible elements for engaging the screw head portion of the bone screw in a locking arrangement with a bone plate such that the flexible elements decrease the outer diameter of the head portion during insertion into a bone plate and expand after insertion is completed thereby locking the screw to the bone plate.

In another embodiment, the invention encompasses a bone screw comprising a screw head and a proximal shaft adapted to be secured to a bone wherein the head comprises a locking cap comprising:

(i) a plurality of fingers projecting upwardly from the shaft forming an inner diameter in the head portion; and (ii) a rotatable locking cap located in said inner diameter of the head portion such that rotation of the locking cap engages the cap with the fingers causing a positive locking feature.

In another embodiment, the invention encompasses a locking bone screw comprising a screw head and a proximal shaft adapted to be secured to a bone wherein the head portion comprises:

(i) an inner bore;

(ii) a plurality of finger elements projecting upwardly from the shaft forming the inner bore with an inner diameter in the head portion; and (iii) a rotatable locking cap located in said inner diameter of the head portion such that rotation of the locking cap engages the cap with the fingers causing a positive locking feature.

In another embodiment, the invention encompasses a locking screw comprising a screw head and a proximal shaft, wherein the screw head comprises an inner bore and collapsible finger elements and an insertable locking plug located in the inner bore of the screw head, wherein the locking plug can be depressed and rotated to engage a positive locking feature.

In another embodiment, the bone screw according to the present invention includes an elongate shaft having a lower threaded body for fixation to a bone. The shaft further has an upper locking structure connected to the threaded body by a neck. The locking structure has an upper end that can be compressed in an inner diameter surrounded by a plurality of finger elements to engage a positive locking feature.

In another embodiment, the invention encompasses a bone screw lock comprising:

(i) a screw head;

(ii) a proximal bone screw hole/plate; and (iii) a locking insert, wherein the screw head is spherical in diameter and is split with a plurality of finger elements, which are capable of deflecting in and out, the bone screw hole is spherical, which matches the screw head such that the screw can be placed into a bone plate at an angle and or provide screw angulation; and the locking insert comprises a shaft that has a plurality of arms that mate with the finger elements that divide the screw head.

In another embodiment, the invention encompasses a method of using a locking bone screw of the invention to secure a bone plate or rod to the screw and a bone.

BRIEF DESCRIPTION OF THE FIGURES

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments, in which.

DETAILED DESCRIPTION OF THE INVENTION

Figure 1:
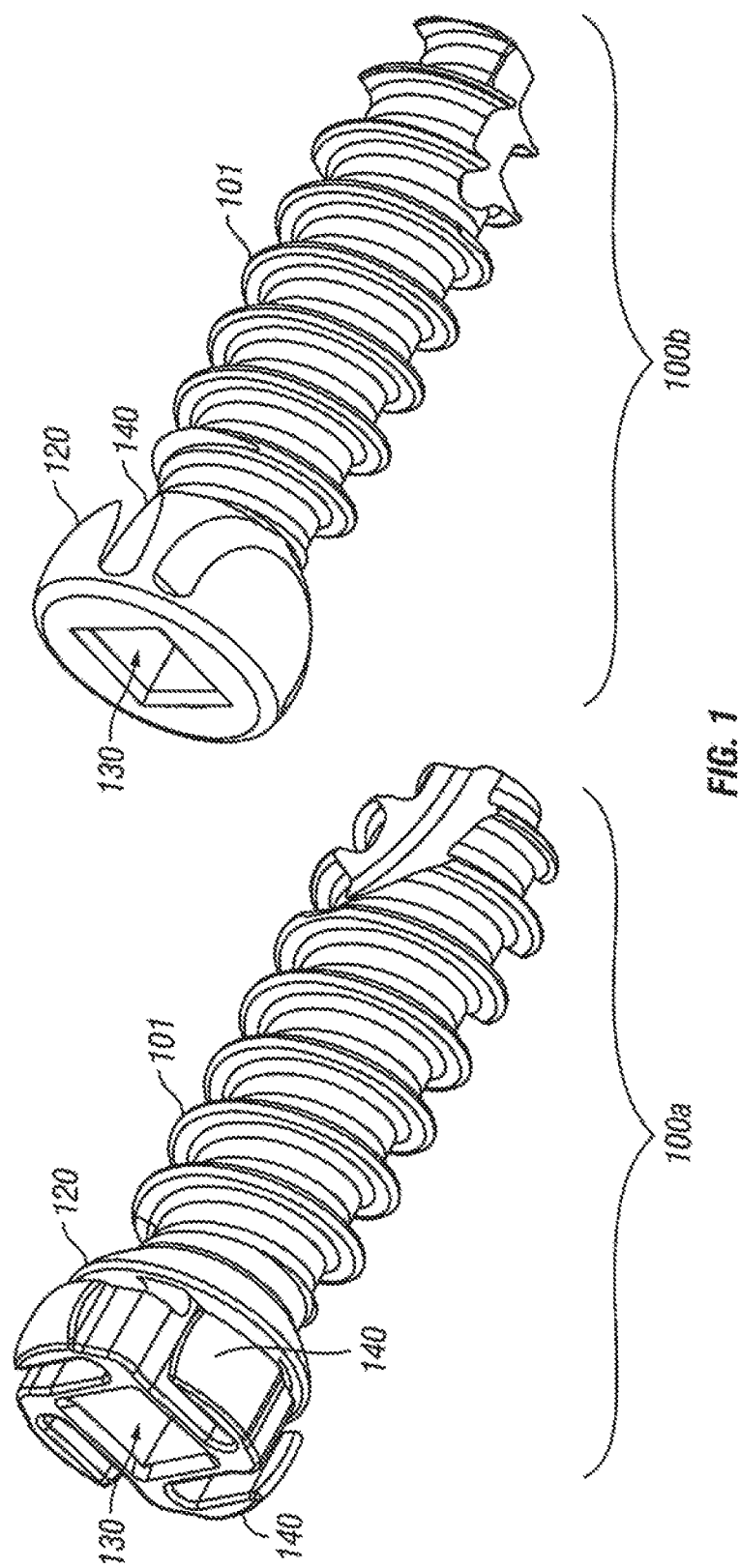
FIG. 1 illustrates a non-limiting, exemplary view of a bone screw of the invention including a flexible locking screw head.

Detailed embodiments of the invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Accordingly, in one embodiment the invention encompasses a locking bone screw comprising a screw head and a proximal shaft adapted to be secured to a bone, wherein the head portion comprises one or more flexible element(s) for engaging the head portion of the bone screw in a locking arrangement with a bone plate such that the flexible elements decrease the outer diameter of the head portion during insertion into a bone plate and allow the head portion to lock to the bone plate.

In certain embodiments, the head portion is substantially spherical.

In certain embodiments, the shaft portion is at least partially threaded.

In certain embodiments, the flexible elements of the head portion comprise tabs for engaging (i.e., locking) with a bone plate.

In certain embodiments, the head portion comprises a square socket driver. In certain embodiments, the screw head comprises a hexagonal socket driver.

In certain embodiments, the flexible elements are configured to lock the bone screw to a fixation rod.

In certain embodiments, the flexible elements further include serrations.

In certain embodiments, the screw head further comprises one or more locking clips. In certain embodiments, the locking clips are configured to engage and lock a bone plate with the screw.

In another embodiment, the invention encompasses a locking bone screw comprising a screw head portion and a proximal shaft adapted to be secured to a bone wherein the head portion comprises (i) an inner bore; (ii) a plurality of finger elements projecting upwardly from the shaft forming the inner bore with an inner diameter in the head portion; and (iii) a rotatable locking cap located in said inner diameter of the head portion such that rotation of the locking cap engages the cap with the finger elements causing a positive locking feature.

In certain embodiments, the shaft is at least partially threaded.

In certain embodiments, a gap exists between the locking cap and fingers when the locking cap is in the unlocked position. In certain embodiments, when the locking cap is in the locked position an interference is caused between the locking cap and finger elements.

In certain embodiments, the locking cap is substantially elliptical.

In certain embodiments, the locking cap is substantially polygonal.

In certain embodiments, the screw head comprises a hexagonal socket driver. In certain embodiments, the screw head comprises a square socket driver.

In certain embodiments, the finger elements are configured to secure the bone screw to a bone plate.

In certain embodiments, the finger elements further include serrations.

In another embodiment, the invention encompasses a locking screw comprising a screw head and a proximal shaft, wherein the screw head comprises an inner bore and collapsible finger elements and a locking plug located in the inner bore of the screw head.

In certain embodiments, the shaft is at least partially threaded.

In certain embodiments, the screw head further comprises smaller diameter screw hole located in the inner bore.

In certain embodiments, the locking plug engages with the screw head portion by inserting the locking plug into smaller diameter screw hole located in the inner bore.

In certain embodiments, the locking plug engages with the screw head portion by pushing the locking plug into the screw head and rotating.

In certain embodiments, the locking plug engages with the screw head portion by rotating the locking plug.

In certain embodiments, the diameter of the inner bore is increased when the screw is in the locked position.

In certain embodiments, the diameter of the inner bore of the screw head is substantially elliptical.

In certain embodiments, the diameter of the inner bore of the screw head is substantially spherical.

In certain embodiments, the head portion comprises a hexagonal socket driver. In certain embodiments, the screw head comprises a square socket driver.

In certain embodiments, the finger elements are configured to lock the bone screw to a bone plate.

In certain embodiments, the fingers further include serrations.

In another embodiment, the invention encompasses a locking bone screw comprising (i) a screw head; (ii) a proximal bone screw hole/plate; and (iii) a locking insert, wherein the screw head is spherical in diameter and is split with a plurality of finger elements, which are capable of deflecting in and out, the bone screw hole in plate is spherical, which matches the screw head such that the screw can be placed into a bone plate at an angle and or provide screw angulation; and the locking insert comprises a shaft that has a plurality of arms that mate with the finger elements that divide the screw head.

In certain embodiments, the screw head is able to flex inward enough to allow the screw to pass through an interference point in the bone screw hole in the plate.

In certain embodiments, the screw head comprises a hex incorporated into it for driving the screw. In certain embodiments, proximal the hex is a groove which creates a cavity that the locking insert communicates, which retains the locking insert in the screw head.

In certain embodiments, the locking insert is a separate component that is assembled into the screw head to provide the screw lock.

In certain embodiments, the core diameter of the locking insert comprises a stop to the screw head and prevents any deflection.

The locking screws of the invention may include polyaxial screws, expandable screws, which when inserted or screwed into the bone and expand by way of some type of expansion mechanism, conventional screws, and the like. In certain embodiments, the screws can be coated with any number of suitable osteoinductive or osteoconductive materials to enhance fixation in the bone. In another embodiment, the screws coating enhance bony in-growth or to further anchor the screw to the bone.

The locking screws may be made from a host of materials. For example, the locking screws may be formed from natural/biological materials, such as allograft, xenograft, and cortical bone. The locking screws may also be formed from synthetic bio-resorbable materials, such as polyanhydride, polyactide, polyglycolide, polyorthoester, polyphosphazene, calcium phosphate, hydroxyapatite, bioactive glass, tyrosine-derived polycabonate, and mixtures thereof.

In other embodiments, the locking screw of the invention is formed of any suitable biocompatible material(s) of sufficient strength to allow the screw to be implanted into a bone. Exemplary biocompatible materials include (1) metals (for example, titanium or titanium alloys, alloys with cobalt and chromium (cobalt-chrome), stainless steel); (2) plastics (for example, ultra-high molecular weight polyethylene (UHMWPE), polymethylmethacrylate (PMMA), polytetrafluoroethylene (PTFE), polyetheretherketone (PEEK), nylon, polypropylene, and/or PMMA/polyhydroxy-ethyl-methacrylate (PHEMA)); (3) ceramics (for example, alumina, beryllia, calcium phosphate, and/or zirconia, among others); (4) composites; (5) bio-resorbable (bioabsorbable) materials or polymers (for example, polymers of alpha-hydroxy carboxylic acids (e.g., polylactic acid (such as PLLA, PDLLA, and/or PDLA), polyglycolic acid, lactide/glycolide copolymers), polydioxanones, polycaprolactones, polytrimethylene carbonate, polyethylene oxide, poly-beta-hydroxybutyrate, poly-.beta.-hydroxypropionate, poly-delta-valerolactone, other bio-resorbable polyesters, and/or natural polymers (such as collagen or other polypeptides, polysaccharides (e.g., starch, cellulose, and/or chitosan), any copolymers thereof); (6) bone tissue (e.g., bone powder and/or bone fragments); and/or the like. The materials may be partially or completely bio-resorbable, as desired or appropriate. In other embodiments, the materials may be partially or completely implantable, as desired or appropriate.

In addition, the locking screws may include growth factors for bone ingrowth and bony attachment, or for soft tissue ingrowth. Non-limiting examples of growth factors include insulin-like growth factor 1, basic fibroblast growth factor, transforming growth factor beta-1, platelet-derived growth factor, bone-derived growth factors, arginine, bone morphogenetic protein, LIM mineralization protein, and combinations thereof.

Referring particularly to FIGS. 1-9 a bone screw is shown which is fabricated of a well known biocompatible material, for example, such as stainless steel, titanium or titanium allow and has a locking screw head and a cylindrical shaft with a tapered a tip remote from the screw head.

With reference to FIG. 1, two bone screws 100a and 100b are shown according to one embodiment of the invention. In this embodiment, the bone screws 100 comprise, concentric to the longitudinal axis of the screw, a screw shaft 101 and a screw head 120, wherein the screw head 120 and optionally the entire screw is made of flexible elements that allow the screw head 120 to temporarily decrease its outer diameter during insertion into, for example, a bone plate. The decrease will allow the screw to pass into the plate and past an otherwise retaining interfering retainment ring.

In certain embodiments, the screws 100a and 100b include a square driver 130 instead of a hexagonal driver to reduce the possibility of the driving geometry stripping.

The bone screws 100a and 100b in certain embodiments also includes tabs 140 in the screw head to allow a more secure or locking fit with a bone plate. For example in certain embodiments, the tabs 140 lock the screw head into fixed frictional contact so as to fix the screw in a one-step lock. In certain embodiments, because of the flexible nature of the screws 100a and 100b, the head 120 and shaft 101 cooperate in such a manner that the head 120 and shaft 101 can be secured at any of a plurality of angles, articulations or rotational alignments relative to one another and within a selected range of angles both from side to side and from front to rear, to enable flexible or articulated engagement until the screw head is locked or fixed with a bone plate near an end of an implantation procedure.

Figure 2A:
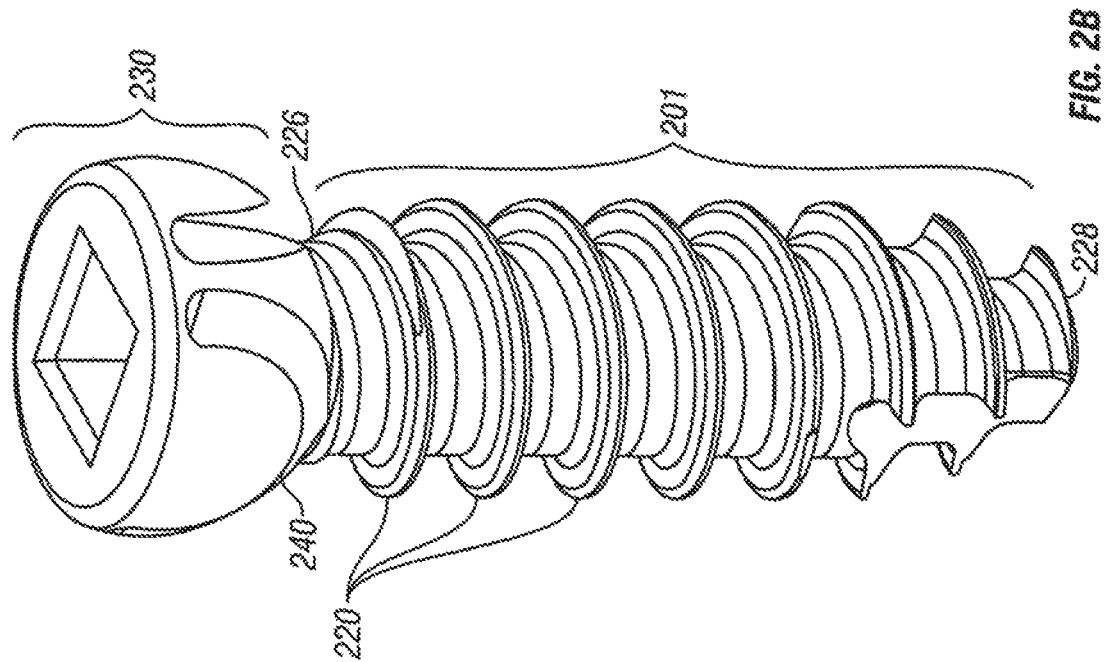
FIGS. 2A and 2B illustrate perspective views of non-limiting, exemplary bone screws of the invention.
Figure 2B:
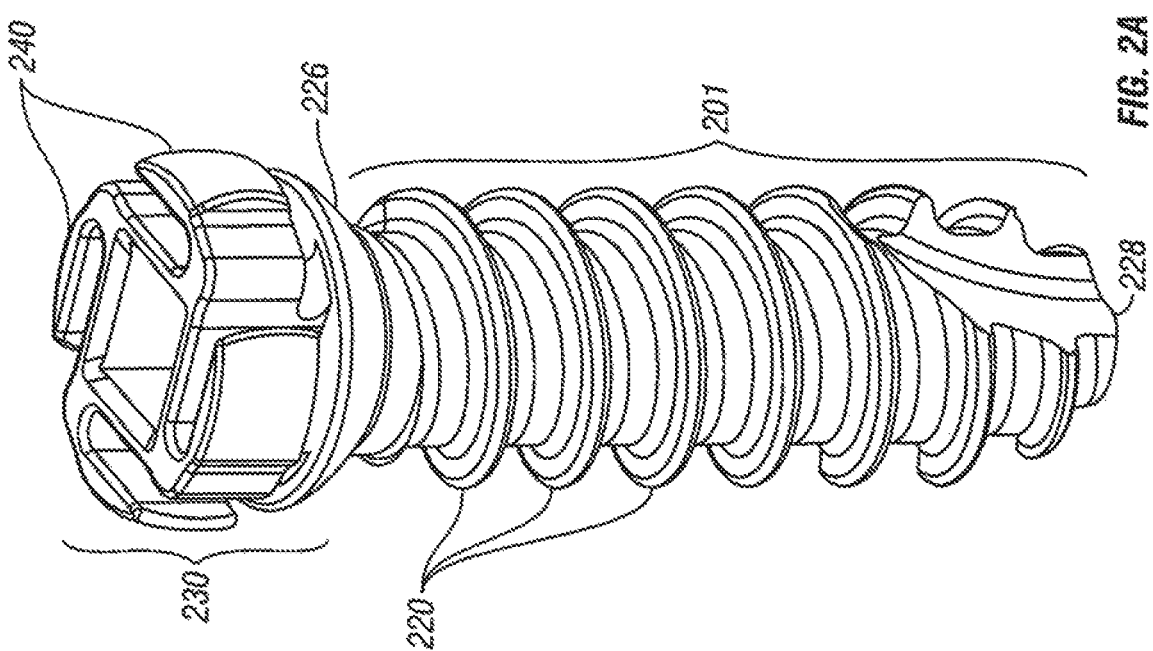

With reference to FIGS. 2a and 2b, the shaft 201 is elongate, with the shaft body having a helically wound bone engaging thread 220 extending from near a neck 226 located adjacent to the screw head to near a tip 228 of the body and projecting radially outward therefrom.

During use, rotation of the body utilizes the thread 220 for gripping and advancement in the bone and is implanted, for example, into a vertebra leading with the tip 228 and driven down into the vertebra with an installation or driving tool, so as to be implanted in the vertebra near the neck 226.

The neck 226 extends axially outward and upward from the shaft body 201 to a flexible locking screw head. The neck 226 generally has a reduced radius as compared to the screw head 230.

The screwhead includes flexible tabs 240 that allow locking with a bone plate.

Figure 3A:
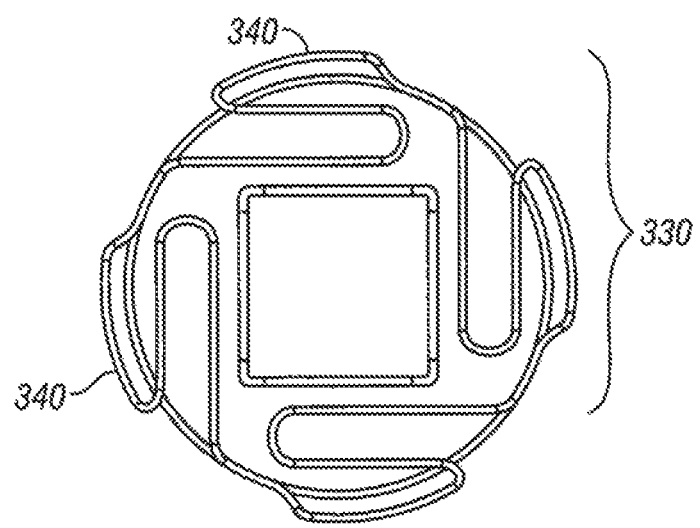
FIG. 3A illustrates a top plan view of non-limiting, exemplary flexible bone screw heads including locking tabs.
Figure 3B:
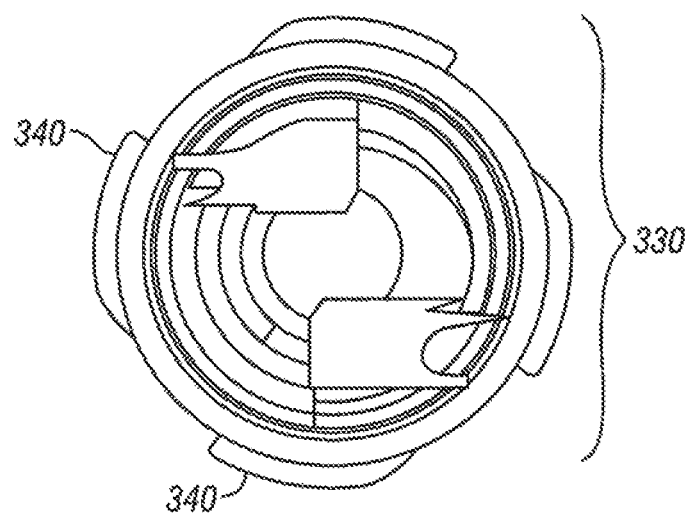
FIG. 3B illustrates a bottom plan view of non-limiting, exemplary flexible bone screw heads including locking tabs.

FIGS. 3A and 3B illustrate top and bottom plan views of the screw. The screw head 330 had flexible tabs 340 protruding from the screw head 330 to pass through a bone plate and thereby lock with the bone plate.

Figure 3C:
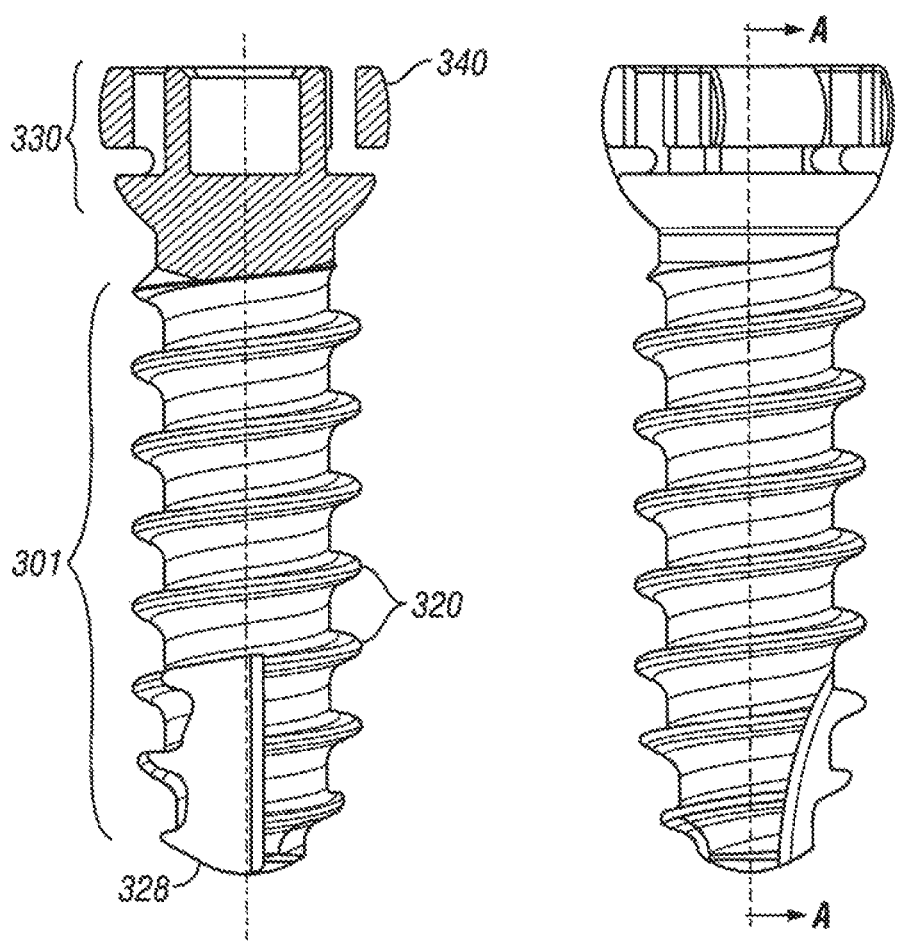
FIG. 3C illustrates a side perspective view of non-limiting, exemplary bone screws.

FIG. 3C illustrates a threaded bone screw including a shaft 301 with threads 320 and a screw head 330 with one or more flexible elements 340 protruding from the screw head and a tapered tip 328 distal from the screw head.

Figure 4A:
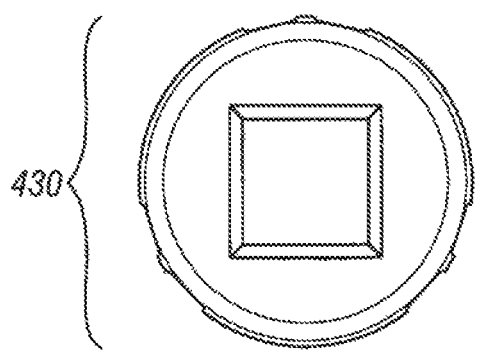
FIG. 4A illustrates a top plan view of a non-limiting, exemplary flexible bone screw head including a square socket driver.
Figure 4B:
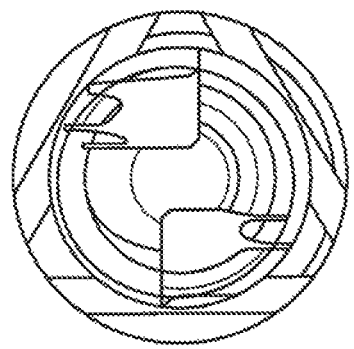
FIG. 4B illustrates a bottom plan view of a non-limiting, exemplary bone screw.

FIGS. 4A and 4B illustrate top and bottom plan views of the screw. The screw head 430 is substantially spherical and flexible in nature to allow the screw head to pass through a bone plate and thereby lock with the bone plate. In an illustrative embodiment, the screw head includes a square driver.

Figure 4C:
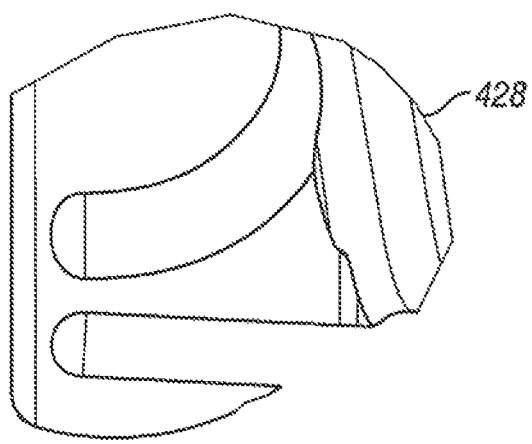
FIG. 4C illustrates a side plan view of a bottom tip of a non-limiting, exemplary bone screw.

FIG. 4C illustrates an illustrative tapered tip portion 428 at the distal end of the shaft opposite the screw head to allow insertion into a bone or callous tissue.

Figure 4D:
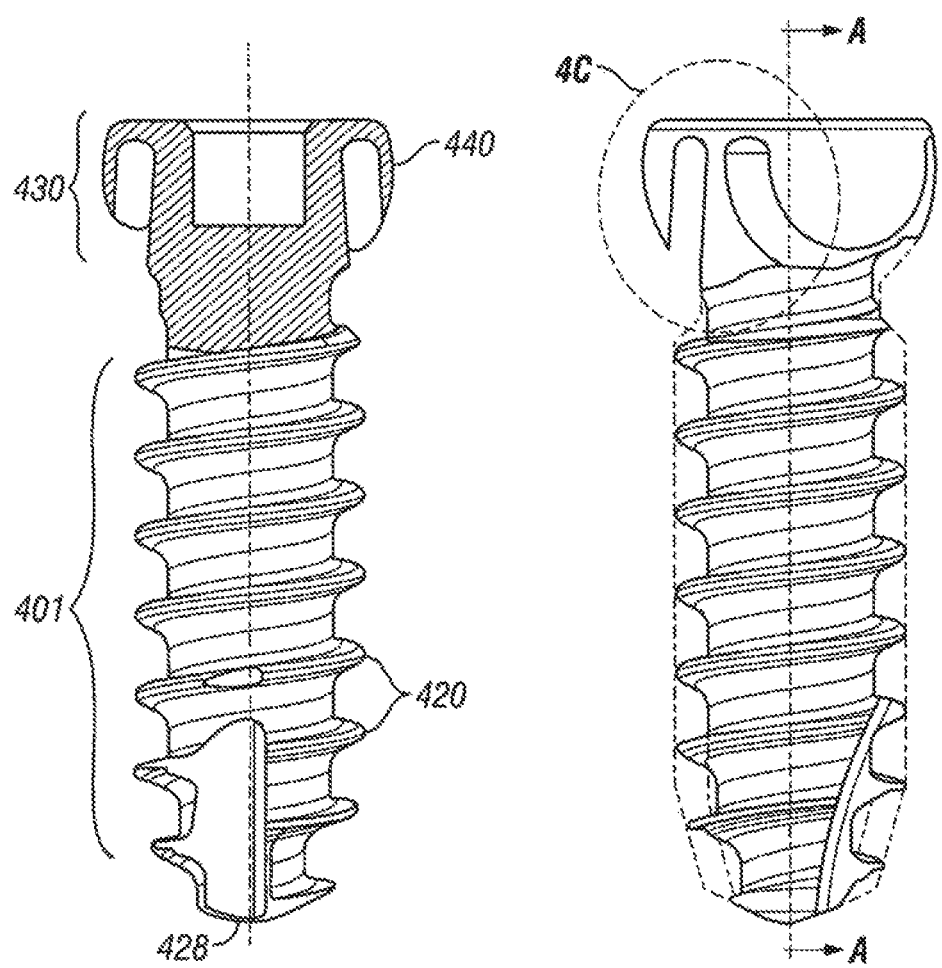
FIG. 4D illustrates side perspective views of non-limiting, exemplary flexible bone screws.

FIG. 4D illustrates a threaded bone screw including a shaft 401 with threads 420 and a screw head 430 with one or more flexible elements 440 protruding from the screw head and a tapered tip 428 distal from the screw head.

Figure 5A:
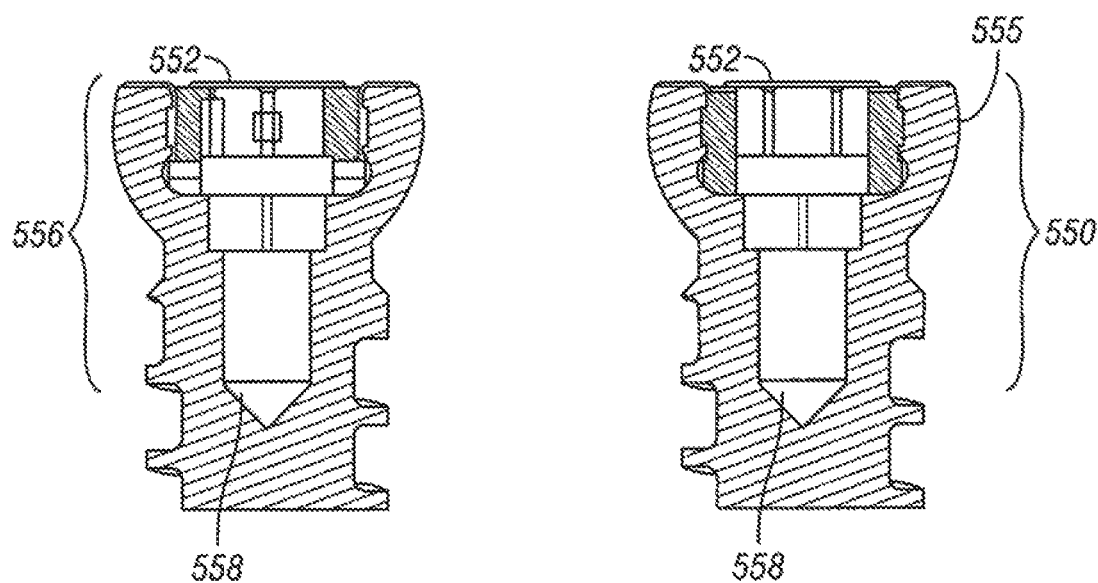
FIG. 5A illustrates cross-sectional views of locking bone screw including an internal locking cap that includes a gap in the unlocked position and an interference in the locked position.

Another embodiment illustrated in FIG. 5A encompasses a bone screw including a distal head portion 550 and a proximal shaft portion (not illustrated) adapted to be secured to a bone and, for example, a bone plate, wherein the screw head 550 comprises (i) a plurality of fingers 555 projecting upwardly from the shaft forming an inner diameter 558 in the head portion and (ii) a rotatable locking cap 552 located in said inner diameter of the head portion such that rotation of the locking cap engages the cap with the fingers causing a positive locking feature (i.e., interference).

The screw head 550 with an inner bore 558 and collapsible fingers elements 555 is optionally pre-assembled with a locking cap 552 capable of inserting into a smaller diameter screw hole.

The inner bore of the screw head allows deflection of the fingers while the screw is inserted into the plate hole. Initially, the locking cap is in position where there is a gap 560 between the cap 552 and the fingers 555. When the locking cap is turned, it adds interference 570 to the screw head, preventing collapse of screw head (fingers) and/or adding interference 570 to increase screw head's spherical diameter thus locking it, for example, with a bone plate.

Figure 5B:
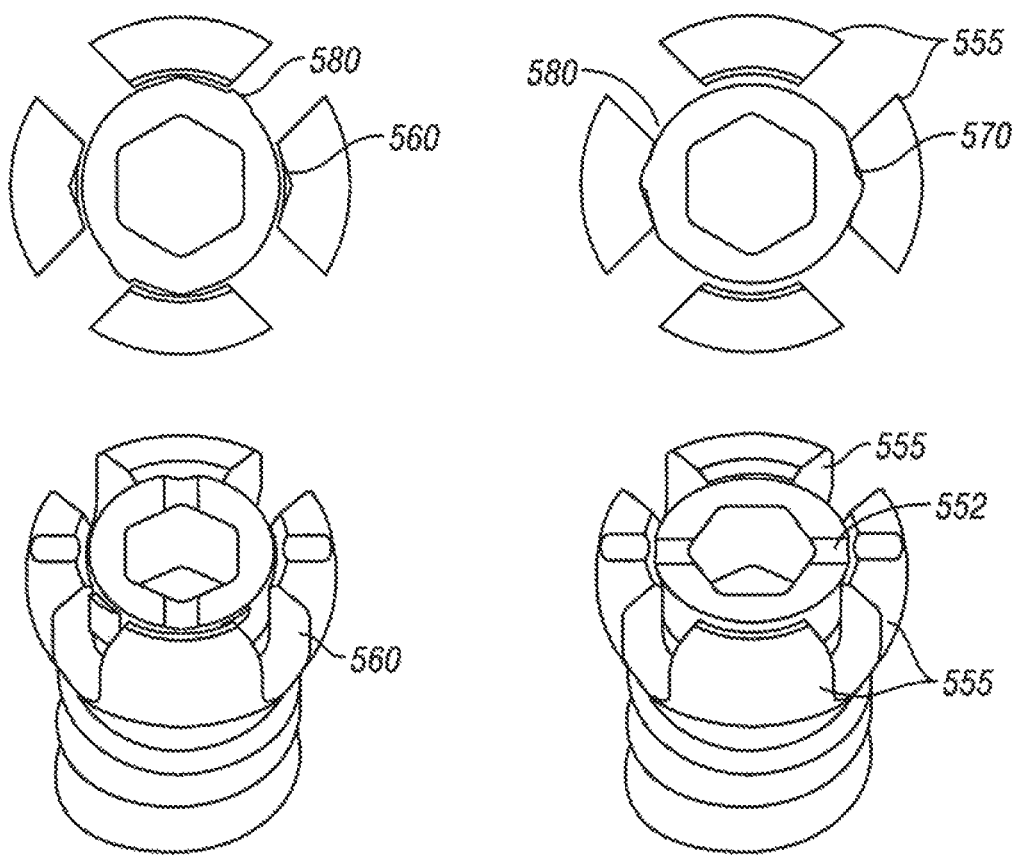
FIG. 5B illustrates a top plan view of non-limiting, exemplary bone screw heads including an elliptical locking cap that can be engaged by rotating the locking cap in a plurality of fingers protruding upwardly from the shaft of the screw.
Figure 5C:
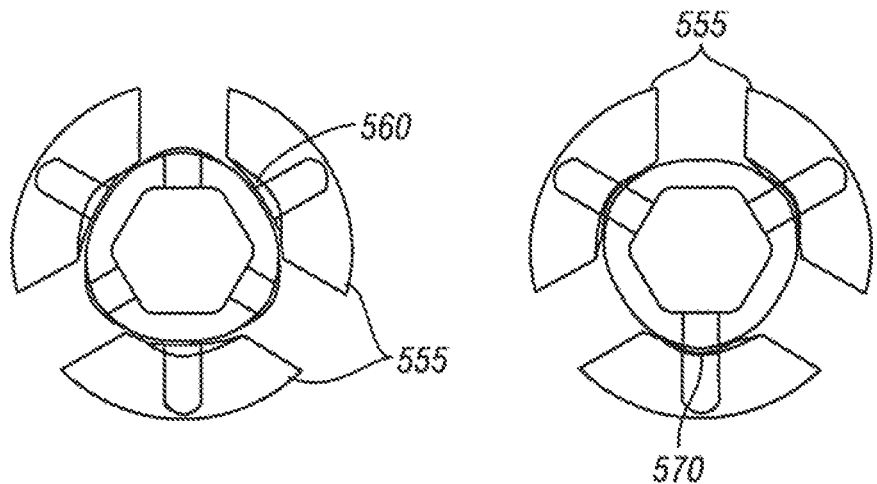
FIG. 5C illustrates a top plan view of non-limiting, exemplary bone screw heads including an polygonal locking cap that can be engages by rotating the locking cap in a plurality of fingers protruding upwardly from the shaft of the screw.

The invention encompasses various different locking caps. FIG. 5B illustrates an elliptical locking cap, and FIG. 5C illustrates a polygonal locking cap.

Initially during insertion of the screw into bone, major and minor diameters of the screw (inner diameter) are aligned with major and minor diameter of the locking cap. There are just enough gaps between elliptical shaped cap and elliptical screw head (inner hole), which allows finger of the screw head to collapse during the screw to plate insertion. Once the screw is seated in the plate, the elliptical head can be turned, for example, about 90° to remove the gap and/or add additional interference to two fingers of the screw head. At this point, major and minor diameter between locking cap and screw is shifted, producing a positive locking feature as illustrated in FIGS. 5B and 5C.

In another illustrative, non-limiting embodiment a polygonal shaped locking cap has side rotates at an angle to add interference to all of the fingers of the screw head. The bumps 580 on the side prevent over turning as illustrated in FIGS. 5B and 5C. (A circlular head is also considered to be a polygon of infinite number of sides).

Figure 5D:
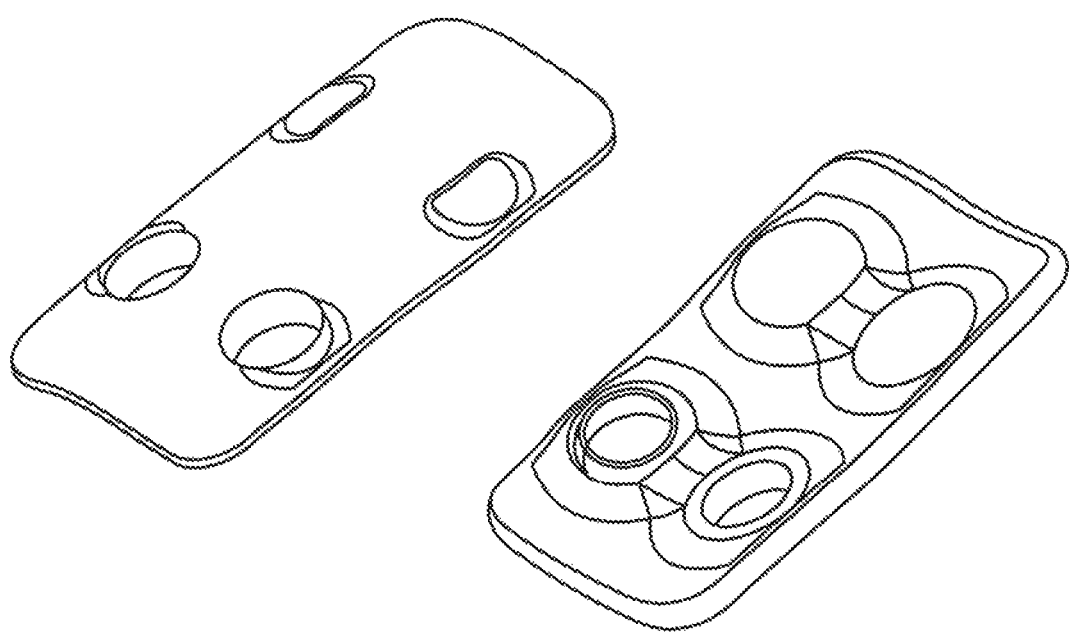
FIG. 5D illustrates an exemplary, non-limiting bone plate that can be utilized with the locking bone screws of the invention.

In various embodiments, the screw applications can also implemented on the thin plate, for example illustrated in FIG. 5D, adding a top and bottom surface bumpers to produce smaller screw entrance.

Advantages of the current locking screw include, but are not limited to, the final product (screw) is one piece design, the screw locking can be done in a single step, screw locking is visible, audible and/or tactile, the invention prevents the screw from going thru the plate, and the screw design can be implemented to the thinner plate design with bump added.

Figure 6A:
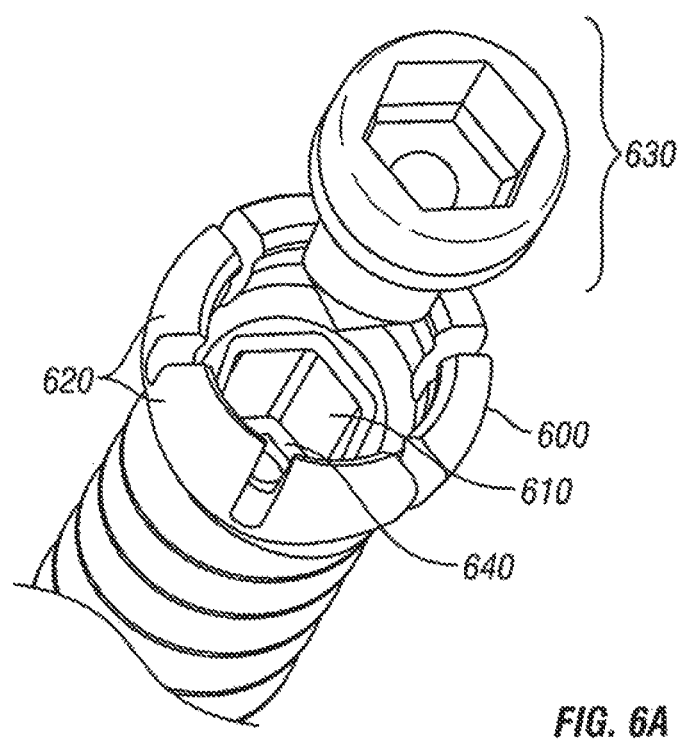
FIGS. 6A and 6B illustrate non-limiting, illustrative embodiments of locking screws comprising a head portion including an inner bore and collapsible finger elements protruding upwardly from the shaft of the screw and a locking plug located in the inner bore of the screw head.

In another embodiment, as illustrated in FIG. 6A, the invention encompasses a screw head 600 with an inner bore 610 and collapsible finger elements 620 is pre-assembled with a Hex locking plug 630, which is capable of fitting into the smaller diameter screw hole 640.

Figure 6B:
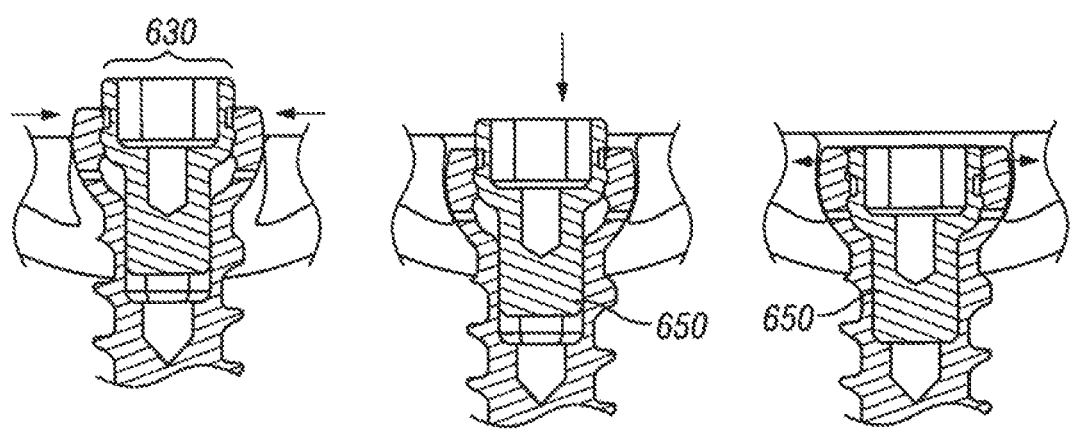

The inner bore 610 of the screw head allows deflection of the fingers while the screw is inserted into the plate hole as illustrated in FIG. 6B. Initially, the locking plug is in position where there is a gap between the plug and the finger elements. The male portion 650 of the locking plug 630 also drives the screw body into the bone. When the screw is fully seated and the locking plug is pushed down (locked) with a low impact push button hex driver, it adds interference to the screw head, preventing collapse of screw head (fingers) and/or increases screw head spherical diameter.

Figure 7:
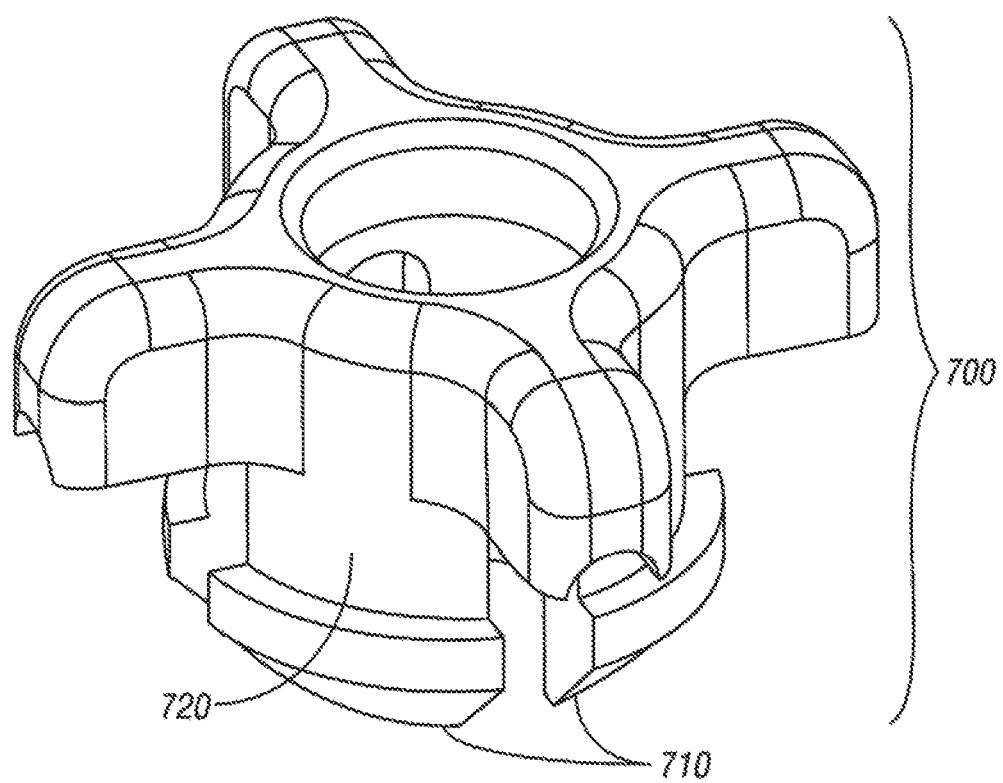
FIG. 7 illustrates a non-limiting, exemplary locking insert, which is spherical in diameter and includes a plurality of fingers, which allow the screw head to deflect in and out to engage a positive locking feature.
Figure 8:
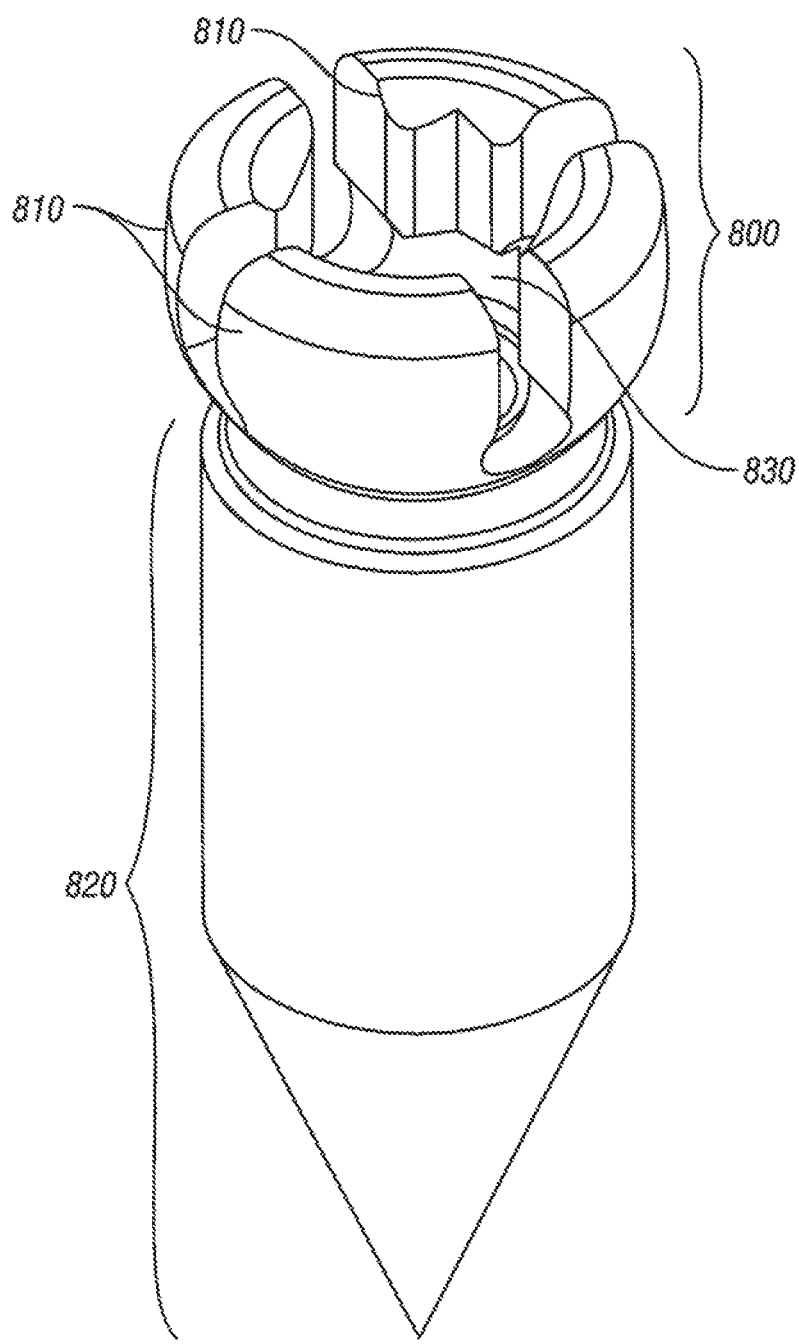
FIG. 8 illustrates a non-limiting, exemplary embodiment of a screw head and a proximal shaft, wherein the screw head comprises four (4) arms that mate with the fingers of the locking insert.

Another embodiment encompasses a locking screw including three pieces: a screw head 800, a plate bone/hole screw 820 illustrated in FIG. 8, and a locking insert illustrated in FIG. 7.

In an illustrative embodiment, the screw head 800 is spherical in diameter and is split with about four (4) finger elements 810, which allow the screw head to deflect in and out. The finger elements 810 are able to flex inward enough to allow the screw to pass through an interference point in the bone screw hole in a bone plate. The screw head also optionally has a hex incorporated into it for driving the screw.

At the bottom of the hex, a groove is placed which creates the cavity 830 that clips 710 of the locking insert 700 snap into, which retains the locking insert in the screw head.

The hole in a bone plate (not illustrated) is spherical, which matches the screw head so that the screw can be placed into the plate at an angle and or provide screw angulation. Closer to the top surface of the plate at the upper portion of the bone screw sphere, a slightly undersized through hole provides the interference to keep the screw retained once the locking insert is engaged.

Figure 9:
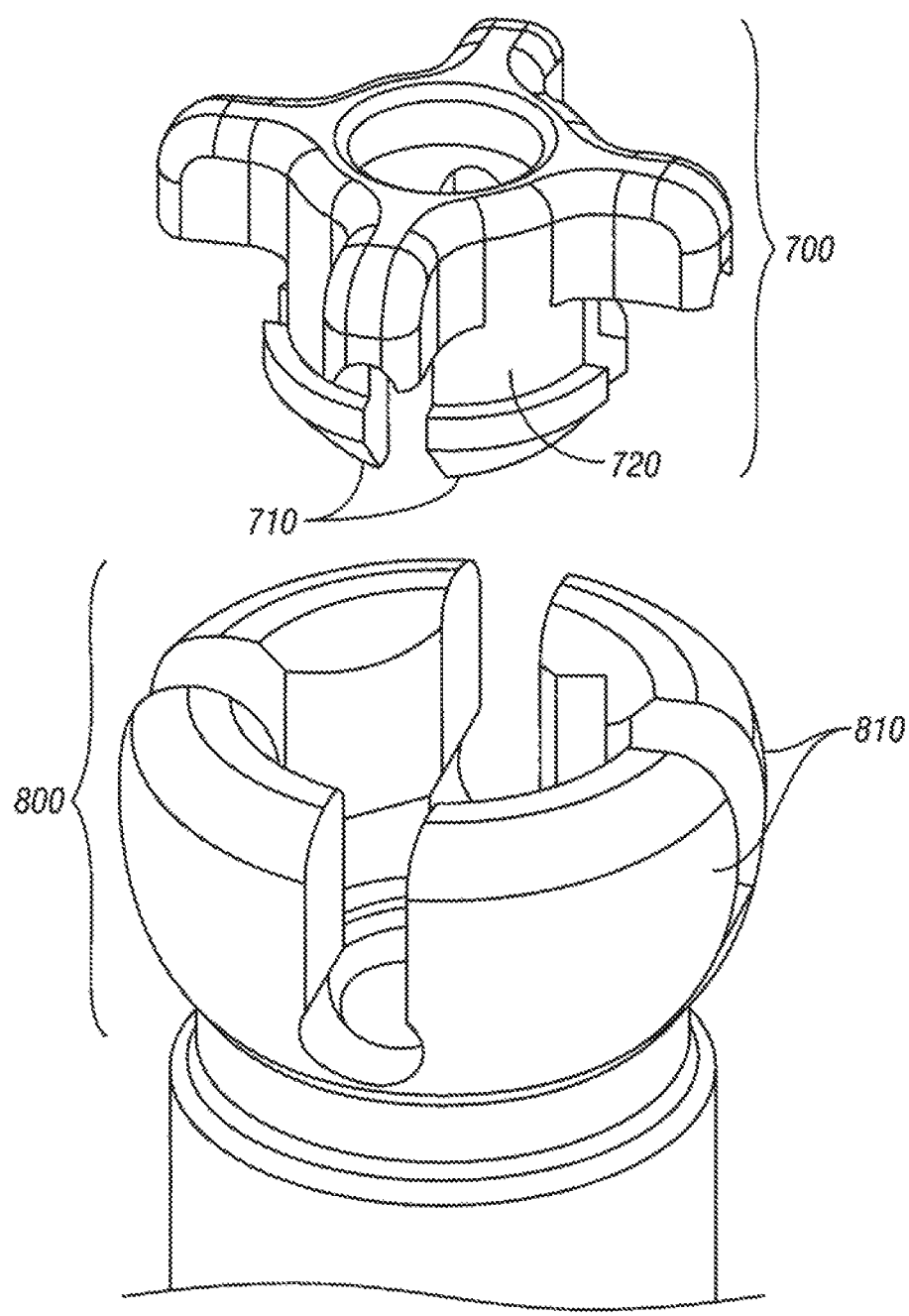
FIG. 9 illustrates a non-limiting, exemplary bone screw locking head comprising (i) a screw head and (ii) a locking insert.

Referring to FIG. 9, the locking insert 700 is a separate component that can be inserted into the screw head to provide the screw lock. The locking insert 700 includes a shaft 720 that comprises a plurality of arms that mate with the finger elements 810. The locking insert 700 has (4) arms 710 extending from the shaft 720 that mate with the finger elements 810 that split the screw head and provide the screw lock. The (4) arms communicate in a locking manner with the finger elements 810 that split the screw head 800. Along with the finger elements 810, the core diameter provides a stop to the screw head and prevents any deflection. The tip of the insert 700 is tapered and is also split (4) ways to allow the insert 700 to snap into the screw head and engage the groove in the bottom of the hex.

The main surgical advantage of the mechanism is that it provides an audible, tactile, and visual indication that the screw is locked, without adding thickness to the plate itself.

This lock fits into the screw head and is low profile. Since it is so easy to install, the second step required to insert the lock is negligible.

This lock can also be removed with the proper instrumentation and will work when the screws are angulated in the plate. The tapered tip on the Locking Insert makes it self-starting and easy to engage.

Since the lock is a separate component, it makes the plates and bone screws easier to machine because usually these locks historically require tedious assembly and or small highly tolerance parts to make them work.

In will be appreciated that different types of screw assemblies can be incorporated with the lock screws of the invention, for example, polyaxial screws. In addition, the screws illustrated herein include threads. It is foreseen that other thread types, such as V-threads, square threads, other inverted thread types or other thread like or non-thread like guide and advancement structures, such as flange form, helically wound advancement structures may be utilized according to the invention. Other preferred thread-types also include square threads with wide strong teeth and greater surface contact as well as modified inverted buttress threads, for example buttress threads wherein the angular relationship between the trailing and leading surfaces are modified somewhat, or wherein the size, shape or orientation of the connecting wall between the leading and trailing surfaces is modified somewhat.

Methods of Use

The invention encompasses a locking screw for use in implantation of screws in a bone cavity of a subject requiring stabilization or immobilization of one or more bones (e.g., vertebrae).

Specifically, the invention encompasses a bone screw for use in the human body including a shaft with a thread along at least a portion of its length and a locking mechanism to secure the screw, for example to a bone plate or rod.

In certain embodiments, the thread has an outer diameter dimensioned to pass through the screw hole in the implant. The trailing end of the screw (e.g., the screw head) is configured to cooperatively engage at least a portion of the screw hole in the plate or rod of the implant so as to prevent the screw from linear motion along the mid-longitudinal axis of the shaft in a direction opposite to the direction of insertion when the screw is secured to the screw hole to attach the implant to a bone portion of the human body.

The locking screw of the invention can be implanted and used to fasten various different types of bones (e.g., hip, femur, vertebra).

In certain embodiments, the invention encompasses a locking bone screw useful for fixing or pre-mounting a fastening device on the bone screw, which can be implanted by minimal invasive surgery where appropriate.

In certain embodiments, included on the locking screw is a fastening device, where the fastening device displays an extension that can engage the bone screw. In other embodiments, the locking screw and the fastening device comprise a single body.

In another embodiment, the invention encompasses methods for treating an subject requiring bone containment comprising:
a. creating a cavity in a vertebral body;
b. inserting into the cavity a locking screw; and
c. attaching a bone plate or rod; and
d. locking the screw to the bone plate.

Kits

The invention also contemplates kits including various locking screws of the invention as wells as the tools needed for surgery, for example, flexible segment portions or rigid rods for use in spinal surgery. The locking screws may be manufactured in varying widths and lengths to accommodate the type of surgery and needs of the surgeon.

The kits of the invention are intended to broaden a surgeon's options once in surgery to provide a patient with the most optimal stabilization system. By containing the most common locking screws, instrument needs and options for assembling actual spine stabilization, the revisions are completed faster and with fewer sets from central supply. Overall, there is less of a labor burden on hospital staff and procedure time is reduced by having all required instruments in one convenient kit.

It is to be understood that while certain forms of the present invention have been illustrated and described herein, it is not to be limited to the specific forms or arrangement of parts described and shown.

In the specification, there have been disclosed typical preferred embodiments of the invention and, although specific terms are employed, they are used in a generic and descriptive sense only and not for purposes of limitation. Obviously many modifications and variations of the invention are possible in light of the above teachings. It is therefore to be understood that the invention may be practiced otherwise than as specifically described.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited above are incorporated herein by reference to the extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A method for stabilizing vertebral bodies comprising the steps of:
providing a locking bone plate;
positioning the locking bone plate on adjacent vertebral bodies;
providing a locking bone screw assembly, the locking bone screw assembly comprising:
a head portion and a shaft portion adapted to be secured to a bone,
wherein the head portion comprises an inner head portion enclosing a driver opening, the inner head portion having outward surfaces, and a plurality of flexible elements extending radially outward from the inner head portion, the flexible elements for engaging an inner surface of a hole in the bone plate in a locking arrangement such that the flexible elements are capable of resiliently deflecting to decrease the outer diameter of the head portion during insertion of the head and shaft portions into the hole in the bone plate and are capable of returning back to an initial position to allow the head portion to lock to the bone plate;
wherein the locking bone screw assembly further comprises a locking insert with a plurality of outward surfaces associated with each of the flexible elements, wherein the flexible elements are configured to deflect inwardly toward the outward surfaces;

wherein in an unlocked position, the locking insert is shaped to have a gap between the outward surfaces and inner surfaces of corresponding flexible elements, and wherein the locking insert is configured to snap into the head portion via one or more locking clips when the locking insert moves from the unlocked position to a locked position; and inserting the shaft portion into the bone through an opening of the locking bone plate.

2. The method of claim 1, wherein the head portion is substantially spherical.

3. The method of claim 1, wherein the shaft portion is at least partially threaded.

4. The method of claim 1, wherein the driver opening is a square.

5. The method of claim 1, wherein the locking insert further includes the one or more locking clips.

6. The method of claim 1, wherein the inner head portion enclosing the driver opening includes a first portion, a second portion connected to the first portion at a first corner, a third portion connected to the second portion at a second corner, a fourth portion connected to the third portion at a third corner, and the fourth portion connected to the first portion at a fourth corner.

7. The method of claim 6, wherein each of the one or more flexible elements extend from a respective one of the first, second, third, or fourth corners of the inner head portion.

8. The method of claim 1, wherein when in the initial position the one or more outward surface and the one or more inward surfaces are substantially parallel to one another.

9. A method for stabilizing vertebral bodies comprising the steps of:

providing a bone plate;

positioning the bone plate on adjacent vertebral bodies; and providing a locking bone screw assembly comprising:

a head portion and a shaft portion adapted to be secured to a bone, wherein the head portion comprises an inner head portion enclosing a driver opening, the inner head portion having outward surfaces, and a plurality of flexible elements extending radially outward from the inner head portion, the flexible elements for engaging an inner surface of a hole in the bone plate in a locking arrangement such that the flexible elements are capable of resiliently deflecting to decrease the outer diameter of the head portion during insertion of the head and shaft portions into the hole in the bone plate and are capable of returning back to an initial position to allow the head portion to lock to the bone plate, wherein the head portion further comprises a locking insert with a plurality of arms, each arm defining a clip at a distal end thereof, wherein the clips snap into the head portion when the locking insert moves from an unlocked position to a locked position; and positioning the locking bone screw assembly within the bone plate.

10. The method of claim 9, wherein the head portion is substantially spherical.

11. The method of claim 9, wherein the shaft portion is at least partially threaded.

12. The method of claim 9, wherein the driver opening is a square.

13. The method of claim 9, wherein the inner head portion enclosing the driver opening includes a first portion, a second portion connected to the first portion at a first corner, a third portion connected to the second portion at a second corner, a fourth portion connected to the third portion at a third corner, and the fourth portion connected to the first portion at a fourth corner.

14. The method of claim 13, wherein each of the one or more flexible elements extend from a respective one of the first, second, third, or fourth corners of the inner head portion.

15. The method of claim 13, wherein when in the initial position the one or more outward surface and the one or more inward surfaces are substantially parallel to one another.

16. The method of claim 9, wherein the head portion includes a groove that receives each of the clips.

* * * * *